US010718708B2

(12) United States Patent
Ushida et al.

(10) Patent No.: US 10,718,708 B2
(45) Date of Patent: Jul. 21, 2020

(54) METHOD FOR OBSERVING DYNAMIC PHYSICAL PROPERTY OF BIOLOGICAL TISSUE AND DEVICE FOR OBSERVING DYNAMIC PHYSICAL PROPERTY OF BIOLOGICAL TISSUE

(71) Applicants: ADVANCED BIO-SPECTROSCOPY CO., LTD, Tokyo (JP); THE UNIVERSITY OF TOKYO, Tokyo (JP)

(72) Inventors: Takashi Ushida, Ibaraki (JP); Katsuko Furukawa, Tokyo (JP); Seizi Nishizawa, Tokyo (JP)

(73) Assignees: ADVANCED BIO-SPECTROSCOPY CO., LTD, Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 16/091,531

(22) PCT Filed: Apr. 4, 2017

(86) PCT No.: PCT/JP2017/014142
§ 371 (c)(1),
(2) Date: Oct. 5, 2018

(87) PCT Pub. No.: WO2017/175770
PCT Pub. Date: Oct. 12, 2017

(65) Prior Publication Data
US 2019/0128803 A1     May 2, 2019

(30) Foreign Application Priority Data
Apr. 5, 2016   (JP) ................................ 2016-075571

(51) Int. Cl.
*G01J 3/447*     (2006.01)
*G01N 21/3586*     (2014.01)
(Continued)

(52) U.S. Cl.
CPC ........... *G01N 21/3586* (2013.01); *A61F 2/08* (2013.01); *A61F 2/468* (2013.01);
(Continued)

(58) Field of Classification Search
CPC .. G01J 3/443; G01J 3/00; G01J 3/4531; G01J 3/4532
See application file for complete search history.

(56) References Cited

U.S. PATENT DOCUMENTS 7,507,966 B2    3/2009   Nishizawa et al.
2006/0278830 A1   12/2006   Nishizawa et al.
(Continued)

FOREIGN PATENT DOCUMENTS

EP      1 801 939 A1    6/2007
JP      2000-275103 A   10/2000
(Continued)

OTHER PUBLICATIONS

Choi et al. "Terahertz Chiroptical Spectroscopy of an a-Helical Polypeptide: A Molecular Simulation Study" J. Phys. Chem. B, Oct. 24, 2014, p. 12837-12843 (Year: 2014).*
(Continued)

*Primary Examiner* — David P Porta
*Assistant Examiner* — Mamadou Faye
(74) *Attorney, Agent, or Firm* — Xsensus LLP

(57) ABSTRACT

An object is to provide a technique that can evaluate biological tissues such as cartilage tissue and regenerated tissues such as regenerated cartilage. A method for observing a dynamic physical property of a biological tissue according to the present invention is that a biological tissue
(Continued)

is irradiated with a pulsed light having a wavelength of a far-infrared wavelength region modulated into circular polarized lights by applying bias voltages to a radiation means (3) having an antenna electrode films of orthogonal (2)-axis structure with phases shifted using high-voltage high-speed modulation means (13), and dynamic physical property of the biological tissue is observed on the basis of a spectrum obtained by vibration optical activity spectroscopy.

12 Claims, 3 Drawing Sheets

(51) Int. Cl.
- *G01N 21/19* (2006.01)
- *G01N 21/21* (2006.01)
- *A61F 2/08* (2006.01)
- *A61F 2/46* (2006.01)
- *A61L 27/36* (2006.01)
- *G01N 33/483* (2006.01)
- *A61F 2/30* (2006.01)

(52) U.S. Cl.
CPC .......... *A61L 27/3612* (2013.01); *G01N 21/19* (2013.01); *G01N 21/21* (2013.01); *G01N 33/4833* (2013.01); *A61F 2002/30762* (2013.01); *A61L 2430/06* (2013.01)

(56) References Cited

U.S. PATENT DOCUMENTS

| | | | |
|---|---|---|---|
| 2007/0194253 A1 | 8/2007 | Nishizawa et al. | |
| 2007/0222988 A1 | 9/2007 | Jiang et al. | |
| 2009/0152469 A1 | 6/2009 | Nishizawa et al. | |
| 2011/0122407 A1* | 5/2011 | Jalali ..................... | G01N 21/65 356/301 |
| 2014/0291524 A1 | 10/2014 | Kubota et al. | |

FOREIGN PATENT DOCUMENTS

| JP | 2001-141567 A | 5/2001 |
|---|---|---|
| JP | 2002-277394 A | 9/2002 |
| JP | 2003-279412 A | 10/2003 |
| JP | 2004-063284 A | 6/2004 |
| JP | 2005-069840 A | 3/2005 |
| JP | 2006-098289 A | 4/2006 |
| JP | 2006-098294 A | 4/2006 |
| JP | 3806742 B2 | 8/2006 |
| JP | 3830483 B2 | 10/2006 |
| JP | 3914553 B2 | 5/2007 |
| JP | 3922463 B2 | 5/2007 |
| JP | 4059403 B2 | 3/2008 |
| JP | 2010-223586 A | 10/2010 |
| JP | 2011-112548 A | 6/2011 |
| JP | 2012-202812 A | 10/2012 |
| JP | 2014-209094 A | 11/2014 |
| JP | 2015-049096 A | 3/2015 |

OTHER PUBLICATIONS

Lombardi et al. "Observation and Calculation of Vibrational Circular Birefringence: A New Form of Vibrational Optical Activity", Wiley Interscience, Dec. 2009, p. E278-E286. (Year: 2009).*

Kan, T., et al., "Enantiomeric switching of chiral metamaterial for terahertz polarization modulation employing vertically deformable MEMS spirals," Nature Communications 6, Article No. 8422, pp. 1-7 (Oct. 1, 2015).

Minamide, H., et al., "A Continuously Tunable Ring-Cavity THz-Wave Parametric Oscillator," The Review of Laser Engineering, vol. 29, Issue 11, pp. 744-748 (Nov. 2001) (English Abstract Only).

Notake, T., et al., "Development of wideband THz-wave spectroscopic stokes-polarimeter," Japan Society of Applied Physics and Related Societies, Extended Abstracts of the 59th Meeting, pp. 04-201 (2012).

English Translation of International Search Report and Written Opinion for International Application No. PCT/JP2017/014142, dated Jul. 4, 2017.

Extended Search Report issued in European Application 17779148.0-1020 dated Nov. 15, 2019.

Elezzabi, A.Y., "Optical Activity in an Artificial Chiral Media: a Terahertz Time-Domain Investigation of Karl F. Lindrnan's 1920 Pioneering Experiment", Optics Express, vol. 17, No. 8, pp. 6600-6612, (Apr. 13, 2009).

Xu, J., et al., "Methodologies arid Techniques for Detecting Extraterrestrial (Microbial) Life", Astrobiology, vol. 3, No. 3, pp. 489-504, (Jan. 1, 2003).

Hirota, Y., et al., "Polarization Modulation of Terahertz Electromagnetic Radiation by Four on a Photoconductive Antenna", Optics Express, vol. 14, No. 10, 8 Pages total, (May 15, 2006).

Aschaffenburg, D.J., et al., "Efficient Measurement of Broadband Terahertz Optical Activity", Appliedphysics Letters, vol. 100, No. 24, 6 Pages total, (Jun. 15, 2012).

* cited by examiner

METHOD FOR OBSERVING DYNAMIC PHYSICAL PROPERTY OF BIOLOGICAL TISSUE AND DEVICE FOR OBSERVING DYNAMIC PHYSICAL PROPERTY OF BIOLOGICAL TISSUE

Technical Field

The present invention relates to a method for observing a dynamic physical property of a biological tissue and a device for observing a dynamic physical property of a biological tissue.

BACKGROUND ART

As society experiences aging of population, the number of patients suffering from diseases of organs of locomotion as represented by locomotive syndrome, in particular joint diseases has been increasing. One of the joint diseases is osteoarthritis. Osteoarthritis is rarely healed spontaneously once a patient develops it, which generally progresses irreversibly and makes it difficult for him/her to walk. Therefore, osteoarthritis is one of the major factors lowering the quality of life of middle-aged and elderly people.

From the viewpoint of, for example, maintenance of the patient's quality of life, there has been increasing needs for early diagnosis and early treatment of osteoarthritis. In recent years, as an early treatment of osteoarthritis, treatment by regenerated cartilage transplantation is performed.

CITATION LIST

Patent Literature

[PTL 1] Japanese Unexamined Patent Application, Publication No. 2001-141567

SUMMARY OF INVENTION

Technical Problem

Regenerated tissue products such as regenerated cartilage involve a unique problem that they cannot be subjected to destruction inspection. As a result, in the current situations, regenerated tissues are transplanted without evaluation of their quality. Accordingly, development of a technique for noninvasively evaluating the regenerated tissues has been sought for.

Cartilage tissues are composed of chondrocytes and an extracellular matrix. In the extracellular matrix, macromolecules such as collagen, hyaluronic acid, sulfated glycosaminoglycan exist. The extracellular matrix constructs highly hydrated tissues by trapping a lot of water molecules and achieves high viscoelasticity of cartilage tissue and the like.

Regenerated cartilage uses chondrocytes collected and cultured from a living body and formed by a three-dimensional culture carrier, the chondrocytes, and the matrix produced by the chondrocytes.

Living tissues such as cartilage tissue and regenerated tissues such as regenerated cartilage are complex in structure and difficult to analyze. Patent Literature 1 discloses techniques for measuring an object to be measured such as a biopolymer which has been difficult to measure by conventional spectroscopic methods. However, in Patent Literature 1, it has not been possible to evaluate biological tissues such as cartilage tissue and regenerated tissues such as regenerated cartilage.

The present invention has been made in view of such circumstances, and it is an object of the present invention to provide a technique capable of evaluating biological tissues such as cartilage tissue and regenerated tissues such as regenerated cartilage.

Solution to Problem

The present invention provides a method for observing a dynamic physical property of a biological tissue by using a pulsed light having a wavelength of a far-infrared wavelength region and observing the dynamic physical property of the biological tissue by vibration optical activity spectroscopy.

A cartilage tissue is a tissue containing a lot of water. Water molecules trapped in the extracellular matrix exist not as free water but as confined water in a state trapped and oriented in macromolecules such as the extracellular matrix.

The inventors of the present invention focused on the fact that the confinement of water molecules appears as a viscosity against the deformation due to compressive stress applied to the cartilage tissue, though that the degree of tissue formation and the dynamic physical property of the cartilage tissue could be estimated by measuring the state of the water molecules in the cartilage tissue, and conducted examinations and experimentations.

Vibration optical activity (abbreviated as VOA) spectroscopy is a scheme for measuring the difference in spectra for left and right circular polarized lights indicated by optically active molecules and examining steric information of molecules together with information on the vibration spectrum.

A terahertz wave resides in the far-infrared region and has good transmittivity to biological tissues. Since terahertz waves overlap with energy bands of intermolecular vibration and intramolecular vibration, it is possible to obtain information on tissue formation of biological tissues including cartilage tissue.

The terahertz wave has low photon energy and difficult to detect because it is hidden by noise in intensity or energy spectrum. As a result of intensive research, the inventors of the present invention have found that by using vibration optical activity spectroscopy in the terahertz band, it is made possible to obtain a spectrum attributable to the motion modes of water molecules (slow Debye relaxation mode, early Debye relaxation mode, intermolecular stretching vibration mode, and intermolecular declination vibration mode).

In accordance with one aspect of the above-described invention, a radiation means is used, which has a photoconductive film receiving a pulse excitation light and generating a photocarrier, a pair of first antenna electrode films formed on the photoconductive film and facing each other via a gap, and a pair or multiple pairs of second antenna electrode films arranged so as to face each other via the gap and arranged so as to have an angle relative to the first antenna electrode films, wherein the radiation means is configured to emit a pulsed light having a wavelength of a far-infrared wavelength region by pulsed laser light irradiation; voltages are applied to the first antenna electrode films and the second antenna electrode films, wherein the voltages have phases and/or frequencies shifted relative to each other; the pulsed light is modulated into left and right circular polarized lights; the biological tissue is irradiated with the circular polarized lights; a time-series signal of a reflected pulsed light reflected by the biological tissue or a transmitted pulsed light transmitted through the biological tissue is detected as a current signal; the current signal is converted into a voltage signal; frequencies of the voltages applied to the first antenna electrode film and the second antenna electrode film is synchronized with a reference signal having a reference frequency such that frequencies of the voltages applied to the first antenna electrode film and the second antenna electrode film become equal to the reference frequency of the reference signal; the voltage signal is extracted; and the dynamic physical property of the biological tissue is observed based on a vibrational circular dichroism spectrum and/or polarization spectroscopy spectrum obtained by converting the voltage signal.

In addition, the present invention provides a device for observing a dynamic physical property of a biological tissue. The device includes a radiation means including a photoconductive film receiving an excitation pulsed laser light and generating a photocarrier and an antenna electrode film formed on the photoconductive film, wherein the radiation means is configured to emit pulsed light having a wavelength of a far-infrared wavelength region by irradiation of the excitation pulsed laser light; a modulation means having a voltage generation unit generating a voltage applied to the antenna electrode film and configured to modulate a pulsed light emitted from the radiation means into left and right circular polarized lights; a holding means by which a biological tissue is held; a detection means including a photoconductive film and an antenna electrode film and configured to receive a time-series signal of a reflected pulsed light reflected by the biological tissue or a transmitted pulsed light transmitted through the sample and output a current signal; a current voltage conversion means configured to convert the current signal into a voltage signal; a lock-in amplifier configured to synchronize a frequency of the voltage of the modulation means with a reference signal having a reference frequency such that the frequency of the voltage of the modulation means becomes equal to the reference frequency of the reference signal and extract the voltage signal; and a control means configured to control modulation of the pulsed light. The antenna electrode film has a pair of first antenna electrode films faced each other via a gap and a pair or multiple pairs of second antenna electrode films arranged so as to face each other via the gap and arranged so as to have an angle relative to the first antenna electrode films. The control means has a function of controlling the modulation means such that voltages are independently applied to the first antenna electrode film and the second antenna electrode film.

Since at least four antenna electrode films (a pair of first, antenna electrode films and a pair of second antenna electrode films) are adopted as the radiation means that emits pulsed light having a wavelength of a far-infrared wavelength region (terahertz wave), pulsed lights having different polarization planes can be simultaneously emitted. By shifting the phases and/or amplitudes relative to each other between the pulsed light emitted from the first antenna electrode film and the pulsed light emitted from the second antenna electrode film by the modulation means, a circular polarized light can be synthesized. The circular polarized lights may include elliptically polarized light. According to such a modulation means, phase, amplitude, and cyclic frequency can be modulated, and the degree of freedom of the polarization pattern is increased. Also, it is possible to simultaneously acquire pieces of data of polarization spectroscopy and circular dichroism spectroscopy.

Since the pulsed light is modulated by the modulation means through application of voltages to the first antenna electrode film and the second antenna electrode film, modulation at ultra-high speed can be achieved compared to conventional chopper control modulation. For example, while the limit in the chopper control was about 1 kHz, it is possible to apply a modulation of about 100 kHz to 1 MHz according to one aspect of the present invention, and the modulation period can be brought close to the time width of the pulsed laser light. As a result, measurement at ultra-high speed becomes possible, and the S/N ratio is improved.

By synchronizing the voltage frequency of the modulation means with the reference signal having the same frequency as that of the modulation means and extracting the voltage signal, the signal is detected with the influence of the background noise decreased.

Advantageous Effects of Invention

According to the present invention, it is made possible to provide a technique for observing the degree of tissue formation and dynamic physical property of biological tissues such as cartilage tissue and regenerated tissues such as regenerated cartilage based on vibration optical activity obtained by using terahertz waves. The technology enables early diagnosis of osteoarthritis by incorporating it into an endoscope.

DESCRIPTION OF EMBODIMENTS

Figure 1:
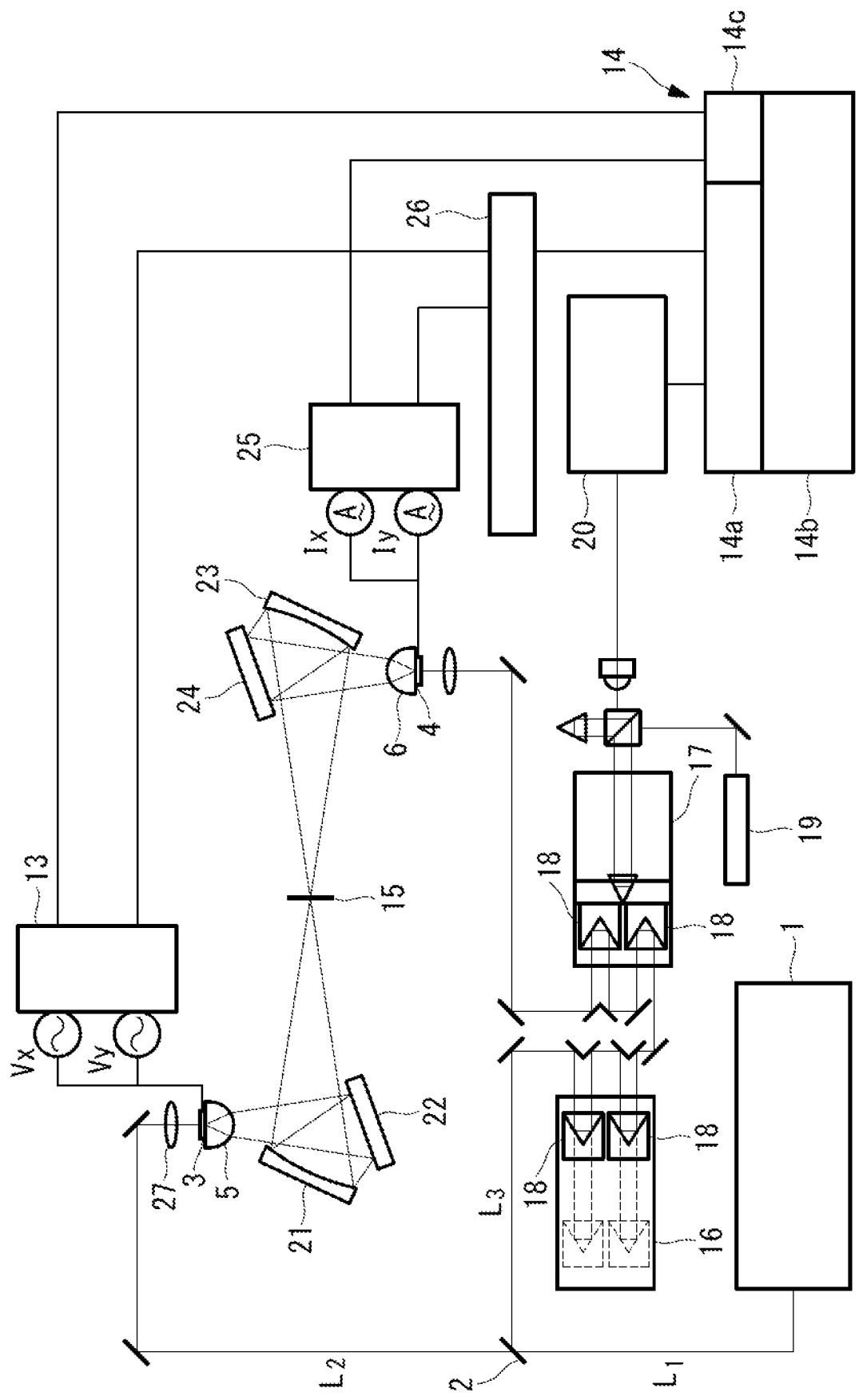
FIG. 1 is a schematic diagram of a device for observing a dynamic physical property of a biological tissue according to one embodiment of the present invention.

FIG. 1 illustrates an example of a device for observing a dynamic physical property of a biological tissue according to the present embodiment.

The device for observing the dynamic physical property of the biological tissue includes a pulsed laser light source 1. An ultrashort pulsed laser is used to configure the pulsed laser light source 1. The ultrashort pulsed laser may include a femtosecond fiber laser, a femtosecond mode-locked titanium sapphire laser, and the like.

The femtosecond fiber laser is configured, for example, by an LD-pumped passive mode-locked fiber laser using a 1.55 μm band erbium (Er) doped fiber laser as a laser gain medium. The femtosecond fiber laser may be an ytterbium (Yb) doped fiber with relatively wide band and high quantum effect around 1.06 μm.

The femtosecond fiber laser is used, for example, at a center oscillation wavelength (second harmonic output) of 780 nm, a pulse width of 120 to 75 fs (femtoseconds), an average output of 30 mw, and a cyclic frequency of around 40 MHz.

In the femtosecond mode-locked titanium sapphire laser, a titanium doped sapphire ($Ti:Al_2O_3$) crystal is used as the laser medium. Titanium doped sapphire crystal is superior for stable oscillation of femtosecond pulses.

The femtosecond mode-locked titanium sapphire laser is used, for example, at a central oscillation wavelength of 780 nm, a pulse width of 100 to 45 fs, an average output of 100 mW, and a cyclic frequency of about 40 to 80 MHz.

In comparison with femtosecond mode-locked titanium sapphire laser, the femtosecond fiber laser has superior advantages in practical use in terms of its small size, light weight, simple stable operation, low cost, and low power consumption. On the other hand, the femtosecond mode-locked titanium-sapphire laser has advantages such as relatively wide spectral bandwidth compared with that of the femtosecond fiber laser, excellent ultrashort pulsed light oscillation, and facilitated high-output oscillation.

The device for observing the dynamic physical property of the biological tissue further includes a beam splitter (splitting means) 2 configured to split the femtosecond laser light (pulsed laser light) $L_1$ emitted from the pulsed laser light source 1 into pulsed laser light $L_2$ for use in excitation and pulsed laser light $L_3$ for use in detection.

The device for observing the dynamic physical property of the biological tissue further includes a terahertz wave generation element (radiation means) 3 configured to emit a pulsed light having a wavelength of a far-infrared wavelength region by irradiation of the pulsed laser light $L_2$ for excitation and a detection element (detection means) 4 configured to detect a time-series signal of the electric field intensity of a transmitted pulsed light (or reflected pulsed light) from the biological tissue irradiated with the pulsed light from the terahertz wave generation element 3. Super-hemispherical silicon lenses 5, 6 are arranged on the light emission side of the terahertz wave generation element 3 and the light incident side of the detection element 4, respectively, as illustrated in FIG. 1.

The terahertz wave generation element 3 and the detection element 4 are photoconductive antenna (abbreviated as PCA) elements. The PCA elements include a photoconductive film and an antenna electrode film.

The photoconductive film is formed, for example, by laminating a thin film of low temperature grown gallium arsenide (abbreviated as LT-GaAs) upon a semi-insulating gallium arsenide (abbreviated as SI-GaAs) substrate.

The antenna electrode film is laminated on the LT-GaAs photoconductive film. The material of the antenna electrode film may include gold (Au), etc. The antenna electrode film can be formed on the LT-GaAs thin layer by a vapor-deposition technique.

Figure 2:
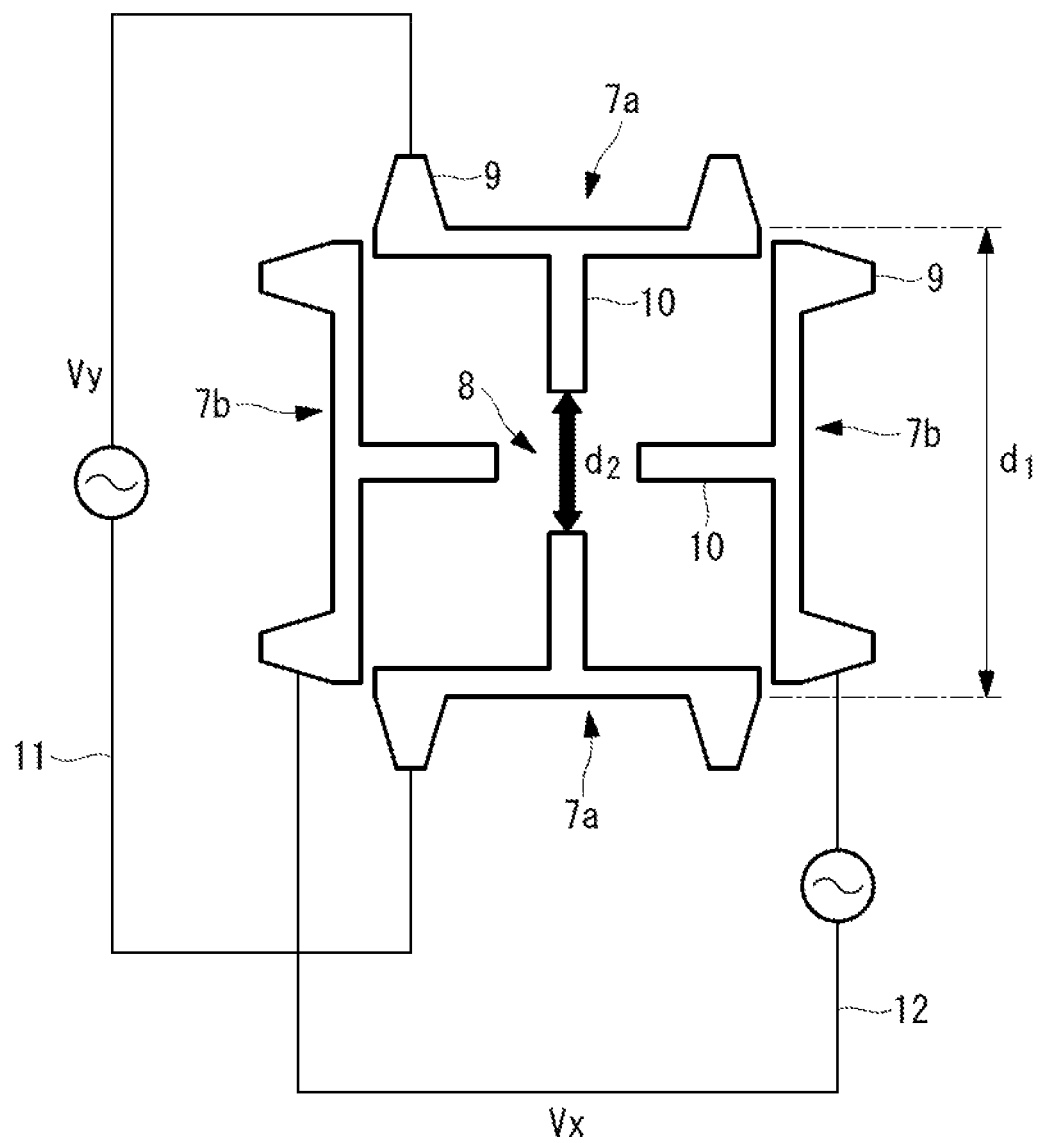
FIG. 2 is a plan view of a pattern of an antenna electrode film.

FIG. 2 is a plan view illustrating a pattern of the antenna electrode film according to the present embodiment. The antenna electrode film is configured by a pair of first antenna electrode films 7a arranged to face each other via a gap 8 and a pair of or multiple pairs of second antenna electrode films 7b arranged to face each other via the gap 8. The gap 8 is shared by the first antenna electrode films 7a and the second antenna electrode films 7b.

The pair of second antenna electrode films 7b is arranged with an angle with respect to the pair of first antenna electrode films 7a. In FIG. 2, the second antenna electrode films 7b in a plan view are arranged with an orientation different by substantially 90 degrees with respect to (substantially orthogonal to) the pair of first antenna electrode films 7a. Specifically, in the antenna electrode film, the pair of first antenna electrode films 7a and the pair of second antenna electrode films 7b have an orthogonal two-axis structure.

The first antenna electrode film 7a and the second antenna electrode film 7b are each configured by a conductive transmission channel 9 and a discharge electrode 10. The tip of the discharge electrode 10 is oriented toward the gap 3.

The pattern of the antenna electrode films can be adopted as appropriate depending on the frequency band of the terahertz wave to be emitted. For example, the outer-path interval $d_1$ of the conductive transmission channel 9 is defined as 30 μm and the gaps $d_2$ of the discharge electrodes 10 facing each other are both defined as 3 μm.

A first lead 11 is connected to the conductive transmission channel 9 of the first antenna electrode film 7a such that voltage can be applied to the pair of first antenna electrode films 7a. A second lead 12 is connected to the conductive transmission channel 9 of the second antenna electrode film 7b such that voltage can be applied to the pair of second antenna electrode films 7b. The other ends of the first, lead and the second lead are connected to the modulation means 13 illustrated in FIG. 1.

The modulation means 13 has a voltage generation device (voltage generation unit) capable of applying bias voltage independently to both the first antenna electrode film 7a and the second antenna electrode film 7b. The modulation means 13 is capable of receiving signals from the control means 14 and modulating the phase, the amplitude, and the cyclic frequency.

A holding means 15 configured to hold a biological tissue (sample) is provided between the terahertz wave generation element 3 and the detection element 4. The term "biological tissue" may include biological tissues such as cartilage tissue and regenerated tissues such as regenerated cartilage.

An optical delay means 16 for time origin adjustment and an optical delay means 17 for time-series signal measurement are arranged on a detection-side optical path extending from the beam splitter 2 to the detection element 4. The order of arrangement of the optical delay means 16 for time origin adjustment and the optical delay means 17 for time-series signal measurement may be inverted.

The optical delay means 16, 17 each include two corner cube mirrors 18. The corner cube mirror 13 is fixed to an automatic feeding stage driven along a single axis and configured to change in a stepwise manner (or successively) the length of the light path from the beam splitter 2 to the detection element 4 by virtue of the stage feeding. The movement of the stage can be measured by the He—Ne laser 19.

The optical delay means 16, 17 having the above-described configuration have the characteristic that the length of the light path can be changed two times as large as that in a case of one single corner cube mirror for scanning of the corner cube mirror. Accordingly, the effect achieved by these means is that it is made possible to specify settings for prompt time origin adjustment and the time-series signal measurement.

A driving device (trigger generation circuit) 20 that automatically carries out scanning is connected to the optical delay means 16 for time origin adjustment and the optical delay means 17 for time-series signal measurement, and the control means 14 that automatically controls the driving device 20 is also connected thereto.

An elliptical mirror (aspherical mirror) 21 and a plane mirror 22 are provided as optical elements on the incidence-side light path between the terahertz wave generation element 3 and the holding means 15. The elliptical mirror 21 is configured to concentrate the pulsed light from the terahertz wave generation element 3. The plane mirror 22 is arranged in the light path between the terahertz wave generation element 3 and the elliptical mirror 21 and has the redirection function for redirecting the pulsed light from the terahertz wave generation element 3. It should be noted that, while one elliptical mirror 21 and one plane mirror 22 are provided as in the case of the present embodiment, multiple elliptical mirrors 21 and multiple plane mirrors 22 can be used in combination.

An elliptical mirror (aspherical mirror) 23 and a plane mirror 24 are provided as optical elements on the detection-side optical path between the detection element 4 and the holding means 15. The elliptical mirror 23 is configured to concentrate the transmitted pulsed light from the sample. The plane mirror 24 is arranged on the light path between the elliptical mirror 23 and the detection element 4, and has the redirection function for redirecting the transmitted pulsed light from the elliptical mirror 23. It should be noted that, while one elliptical mirror 23 and one plane mirror 24 are provided as in the case of the present embodiment, multiple elliptical mirrors 23 and multiple plane mirrors 24 can be used in combination.

A current voltage conversion means (AVC) 25 is connected to the detection element 4. The AVC 25 is configured to convert the current signal that has beers detected by the detection element 4 into a voltage signal.

A control means 14 is connected to the modulation means 13 and the current voltage conversion means 25 directly and via the lock-in amplifier 26. The control means 14 is capable of controlling the application of voltage to the antenna electrode films by the modulation means 13.

The control means 14 includes an analog-to-digital (A/D) converter 14a, an information processing unit 14b, and an input/output unit 14c. The information processing unit 14b is configured by, for example, a central processing unit (CPU), a random access memory (RAM), a read only memory (ROM), a computer readable storage medium, and the like. In addition, the series of processes for realizing the various functions are as an example stored in a storage medium or the like in the form of a program, and the various functions are realized by the CPU reading the program from the RAM or the like and carrying out information processing and arithmetic processing. It should be noted that various modes may be implemented for the program, such as a mode according to which the program is installed in advance in the ROM or another storage medium, a mode according to which the program is provided in a state where the program is stored in a computer-readable storage medium, and a mode according to which the program is distributed by wired or wireless communication means. The computer-readable storage medium refers to a magnetic disk, a magneto-optical disk, a CD-ROM disc, a DVD-ROM disc, a semiconductor memory, and the like.

Next, the operation of the device for observing the dynamic physical property of the biological tissue according to the present embodiment will be described.

The pulsed laser light $L_1$ emitted from the pulsed laser light source 1 is split by the beam splitter 2 into the pulsed laser light (pump pulsed light) $L_2$ for use in excitation and the pulsed laser light (sampling pulsed light) $L_3$ for use in detection.

The excitation pulsed laser light $L_2$ is emitted via the lens 27 to the terahertz wave generation element 3. At this point, the excitation pulsed laser light $L_2$ is concentrated onto the photoconductive film provided in the gap 8 of the antenna electrode film. In a state where bias voltage is applied to the antenna electrode film, when the photoconductive film is irradiated with the excitation pulsed laser light $L_2$, the current due to the light excitation flows instantaneously, and a far-infrared electromagnetic pulse (pulsed light) is emitted.

Figure 3:
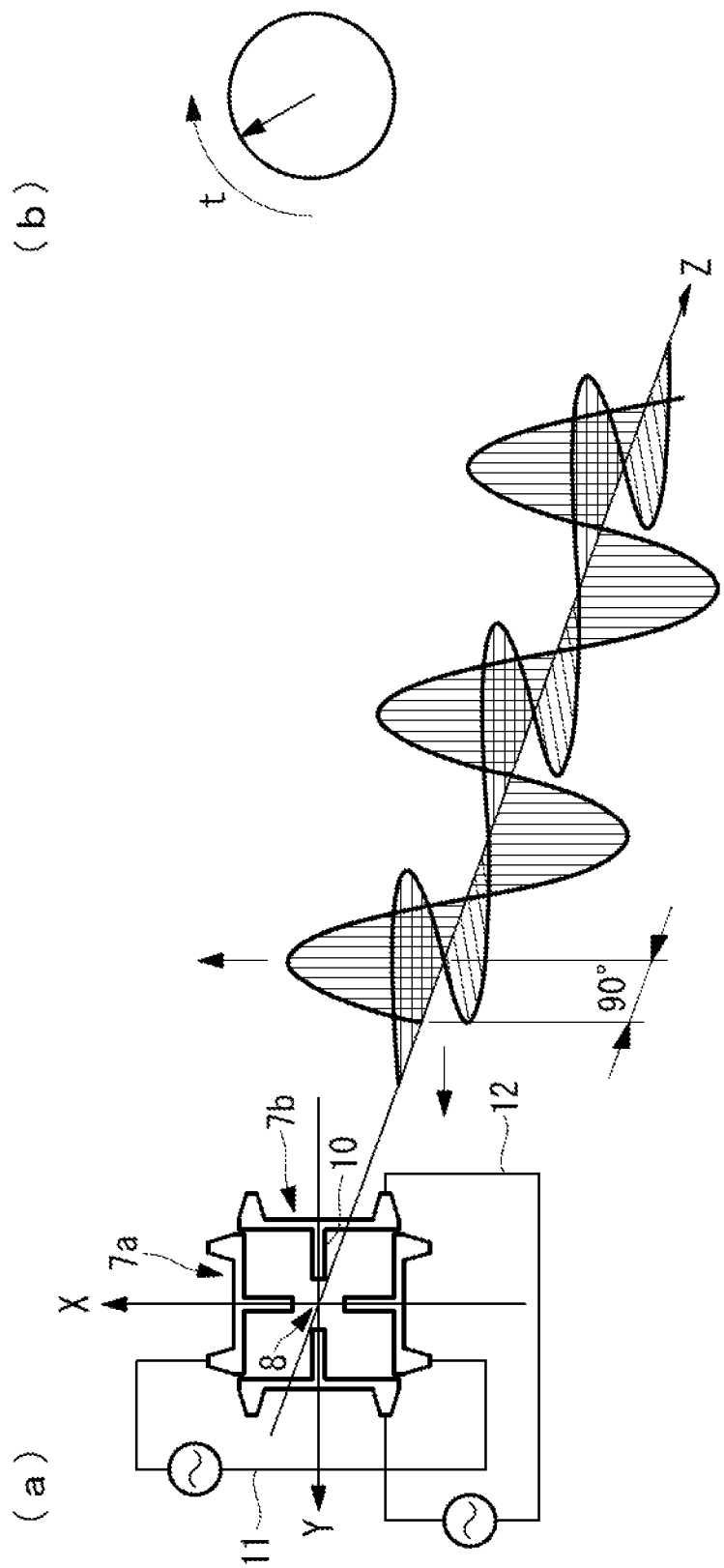
FIG. 3 is a diagram illustrating a polarized pulsed light.

At this point, the modulation means 13, in accordance with a command issued from the information processing unit 14b, simultaneously applies bias voltages to the first antenna electrode film 7a and the second antenna electrode film 7b, where the bias voltages have the same amplitude and period but the different phases shifted relative to each other, and modulates the pulsed light into a circular polarized light (see (a) and (b) of FIG. 3).

When not only the phase but the amplitude of the sinusoidal voltage applied to the second antenna electrode film 7b are differentiated, the pulsed light in the form of an elliptically polarized light will be emitted. By such a use, vibrational circular dichroism measurement can be performed.

The pulsed light, after its light path is redirected by the plane mirror 22, is guided to the elliptical mirror 21, concentrated, and the sample is irradiated therewith.

The transmitted pulsed light that has transmitted the sample with and carries the optical information of the sample (or a reflected pulsed light that has been reflected by the sample) is reflected by the elliptical mirror 23 and then redirected by the plane mirror 24, and further guided to the detection element 4. At this point, the reflected or transmitted pulsed light is concentrated onto the photoconductive film residing in the gap 3 of the antenna electrode films.

The detection pulsed laser light $L_3$ resulting from the splitting by the beam splitter 2 is given a delay time difference at predetermined time intervals by the optical delay means 16 for time origin adjustment and the optical delay means 17 for time-series signal measurement and guided to the detection element 4. At this point, the detection pulsed laser light $L_3$ is concentrated onto the photoconductive film residing in the gap 8 of the antenna electrode films, and superposed on the reflected or transmitted pulsed light of the sample.

The detection element 4 will exhibit conductivity for the moment during which the photoconductive film is irradiated with the detection pulsed laser light $L_3$. Hence, the electric field intensity and the phase lead of the reflected or transmitted pulsed light from the sample to which a trigger is applied and which has arrived at the moment at which the detection element 4 has become conductive are detected as the current signal.

The current signal that has been detected by the detection element 4 is converted into a voltage signal and amplified by the current voltage conversion means 25 and the voltage signal is sent to the lock-in amplifier 26. The pulsed light emitted from the terahertz wave generation element 3 is modulated by the modulation means 13, and the lock-in amplifier 26 uses the cyclic frequency of the modulated pulsed light as the reference signal, picks up only the voltages synchronized with the reference signal using a frequency filter, and the signal is detected with the influence of the background noise decreased.

The voltage signal that has been amplified by the lock-in amplifier 26 is converted into a digital signal by the A/D converter 14a. The information processing unit 14b performs Fourier transformation on the digital signal and calculates the amplitude of the electric field intensity and the spectroscopic spectrum of the phase of the reflected or transmitted pulsed light of the sample.

The control means 14 obtains the polarization spectrum by standardizing spectroscopic spectra that have been obtained or obtaining the difference of them using the spectrum in a case where the sample does not exist. The control means 14 obtains the vibrational circular dichroism spectrum (VCD spectrum) by obtaining the difference of the left and right polarized lights of the spectroscopic spectra that have been obtained. The control means 14 can obtain the dynamic physical property of the sample based on the polarization spectrum and the vibrational circular dichroism spectrum that have been obtained, and observe them. The dynamic physical property may include elastic modulus (η), dielectric constant (ε), relaxation time (T1), refractive index.

As has been described in the foregoing, according to the device for observing the dynamic physical property of the biological tissue in accordance with the present embodiment, since the respective pairs of the antenna electrode films are arranged so as to have different angles, a pulsed light having an appropriate polarization plane can be emitted without the need of rotating the terahertz wave generation element 3, and without the need of arranging a polarization element on the light path. Accordingly, it is made possible to achieve polarization of the pulsed light using a simple structure and without causing the loss of the pulsed light.

Since the modulation means 13 is capable of modulating pulsed light by electronic control by the control means 14, the degree of freedom of the polarization pattern is high.

REFERENCE SIGNS LIST 1 pulsed laser light source
2 beam splitter (splitting means)
3 terahertz wave generation element (radiation means)
4 detection element (detection means)
5, 6 super-hemispherical silicon lens
7a first antenna electrode film
7b second antenna electrode film
8 gap
9 conductive transmission channel
10 discharge electrode
11 first lead
12 second lead
13 modulation means
14 control means
14a A/D converter
14b information processing unit
14c input/output unit
15 holding means
16 optical delay means (for time origin adjustment)
17 optical delay means (for time-series signal measurement)
18 corner cube mirror
19 He—Ne laser
20 driving device (trigger generation circuit)
21, 23 elliptical mirror (aspherical mirror)
22, 24 plane mirror
25 current voltage conversion means
26 lock-in amplifier
27 lens

The invention claimed is:

1. A method for observing a dynamic physical property of a biological tissue, the method comprising:
 observing at least one of elastic modulus, dielectric constant, relaxation time, or refractive index of a biological tissue, as a dynamic physical property of the biological tissue, through vibrational circular dichroism measurement by vibration optical activity spectroscopy using a pulsed light having a wavelength of a far-infrared wavelength region.

2. The method for observing the dynamic physical property of the biological tissue according to claim 1, the method comprising:
 emitting the pulsed light using a light source, the light source including
  a photoconductive film receiving a pulse excitation light and generating a photocarrier,
  a pair of first antenna electrode films formed on the photoconductive film and facing each other via a gap, and
  a pair or multiple pairs of second antenna electrode films arranged so as to face each other via the gap and arranged so as to have an angle relative to the first antenna electrode films;
 applying voltages simultaneously to the first antenna electrode films and the second antenna electrode films, wherein the voltages have phases shifted relative to each other, to modulate the pulsed light into left and right circular polarized lights;
 irradiating the biological tissue with the circular polarized lights;
 detecting, as a current signal, a time-series signal of a reflected pulsed light reflected by the biological tissue or a transmitted pulsed light transmitted through the biological tissue;
 converting the current signal into a voltage signal;
 synchronizing frequencies of the voltages applied to the first antenna electrode film and the second antenna electrode film with a reference signal having a reference frequency such that frequencies of the voltages applied to the first antenna electrode film and the second antenna electrode film become equal to the reference frequency of the reference signal and extracting the voltage signal; and
 observing the dynamic physical property of the biological tissue based on a vibrational circular dichroism spectrum and/or polarization spectroscopy spectrum obtained by converting the voltage signal.

3. A device for observing a dynamic physical property of a biological tissue, the device comprising
 a light source including
  a photoconductive film receiving an excitation pulsed laser light and generating a photocarrier and
  an antenna electrode film formed on the photoconductive film, and configured to emit pulsed light having a wavelength of a far-infrared wavelength region by irradiation of the excitation pulsed laser light;
 a modulation circuit having a voltage generation circuit generating a voltage applied to the antenna electrode film and configured to modulate a pulsed light emitted from the light source into left and right circular polarized lights;
 a holder configured to hold a biological tissue;
 a detector including a photoconductive film and an antenna electrode film and configured to receive a time-series signal of a reflected pulsed light reflected by the biological tissue or a transmitted pulsed light transmitted through the biological tissue and output a current signal;
 a current voltage conversion circuit configured to convert the current signal into a voltage signal;
 a lock-in amplifier configured to synchronize a frequency of the voltage of the modulation circuit with a reference signal having a reference frequency such that the frequency of the voltage of the modulation circuit becomes equal to the reference frequency of the reference signal and extract the voltage signal; and
 a control circuit configured to control modulation of the pulsed light, wherein
 the antenna electrode film has a pair of first antenna electrode films faced each other via a gap and a pair or multiple pairs of second antenna electrode films arranged so as to face each other via the gap and arranged so as to have an angle relative to the first antenna electrode films, the control circuit is configured to control the modulation circuit such that voltages are independently applied to the first antenna electrode film and the second antenna electrode film, and the pulse light having the wavelength of the far-infrared wavelength region is used to observe at least one of elastic modulus, dielectric constant, relaxation time. or refractive index of the biological tissue, as dynamic physical properties of the biological tissue, through vibrational circular dichroism measurement by vibration optical activity spectroscopy.

4. The method according to claim 1, wherein the pulsed light is an elliptically polarized light, and the method further comprises:

emitting the elliptically polarized light; and irradiating the biological tissue with the elliptically polarized light.

5. The method according to claim 1, the method further comprising:

measuring a difference in spectra for left and right circular polarized lights indicated by optically active molecules of the biological tissue in response to emitting the pulsed light.

6. The device according to claim 3, wherein the pulsed light is an elliptically polarized light, and the light source is configured to irradiating the biological tissue with the elliptically polarized light.

7. The device according to claim 3, wherein the control circuitry is configured to measure a difference in spectra for left and right circular polarized lights indicated by optically active molecules of the biological tissue in response to emitting the pulsed light.

8. The method according to claim 1. wherein the observing observes the elastic modulus of the biological tissue, as the dynamic physical property of the biological tissue, through the vibrational circular dichroism measurement.

9. The method according to claim 1, wherein the observing observes the dielectric constant of the biological tissue, as the dynamic physical property of the biological tissue, through the vibrational circular dichroism measurement.

10. The method according to claim 1, wherein the observing observes the relaxation time of the biological tissue, as the dynamic physical property of the biological tissue, through the vibrational circular dichroism measurement.

11. The method according to claim 1, wherein the observing observes the refractive index of the biological tissue, as the dynamic physical property of the biological tissue, through the vibrational circular dichroism measurement.

12. The method according to claim 1, wherein the biological tissue is at least one of a cartilage tissue or a regenerated cartilage.

\* \* \* \* \*